(12) United States Patent
Hua (10) Patent No.: US 9,919,146 B2
(45) Date of Patent: Mar. 20, 2018

(54) METHODS AND SYSTEMS FOR INTRAVENTRICULAR BRAIN STIMULATION

(71) Applicant: Sherwin Hua, Hillsborough, CA (US)

(72) Inventor: Sherwin Hua, Hillsborough, CA (US)

( * ) Notice: Subject to any disclaimer, the term of this patent is extended or adjusted under 35 U.S.C. 154(b) by 465 days.

(21) Appl. No.: 14/266,732

(22) Filed: Apr. 30, 2014

(65) Prior Publication Data

US 2015/0011927 A1 Jan. 8, 2015

Related U.S. Application Data

(60) Provisional application No. 61/818,312, filed on May 1, 2013.

(51) Int. Cl.
*A61M 27/00* (2006.01)
*A61N 1/05* (2006.01)
*A61N 1/36* (2006.01)

(52) U.S. Cl.
CPC .......... *A61N 1/0534* (2013.01); *A61N 1/0529* (2013.01); *A61N 1/36064* (2013.01); *A61N 1/36067* (2013.01); *A61N 1/36082* (2013.01)

(58) Field of Classification Search
None
See application file for complete search history.

(56) References Cited

U.S. PATENT DOCUMENTS

| 5,411,546 | A | 5/1995 | Bowald et al. | |
|---|---|---|---|---|
| 5,531,779 | A | 7/1996 | Dahl et al. | |
| 6,445,953 | B1 | 9/2002 | Bulkes et al. | |
| 6,665,562 | B2 * | 12/2003 | Gluckman | A61N 1/36014 128/898 |
| 6,978,180 | B2 * | 12/2005 | Tadlock | A61N 1/0529 607/2 |
| 7,209,787 | B2 * | 4/2007 | DiLorenzo | A61N 1/3605 607/45 |
| 7,684,867 | B2 * | 3/2010 | Jaax | A61M 5/14276 607/45 |
| 7,917,230 | B2 | 3/2011 | Bly | |
| 7,974,696 | B1 * | 7/2011 | DiLorenzo | A61B 5/0476 607/2 |

(Continued)

OTHER PUBLICATIONS

Koivisto, A.M. et al (2013) Poor Cognitive Outcome in Shunt-Responsive Idiopathic Normal Pressure Hydrocephalus. Neurosurgery 72(1):1-8.

(Continued)

*Primary Examiner* — Brian T Gedeon
(74) *Attorney, Agent, or Firm* — Knobbe, Martens, Olson & Bear LLP (57) ABSTRACT

The present application is directed to devices and methods that can treat dementia or other brain disorders via electrical stimulation. Embodiments disclosed herein utilize brain stimulation of brain areas involved in memory and cognition through an intraventricular approach. Brain stimulation is combined with CSF flow in an intraventricular electrode having one or more passageways to permit fluid to flow therethrough. For example, an intraventricular electrode shunt catheter can be safely placed in any part of the ventricular system and through any foramen or aqueduct of the ventricular system without fear of obstruction to CSF flow.

13 Claims, 8 Drawing Sheets

(56) References Cited

U.S. PATENT DOCUMENTS

| | | | |
|---|---|---|---|
| 8,000,795 B2 | 8/2011 | Lozano | |
| 8,052,711 B2 | 11/2011 | Hanse et al. | |
| 8,103,350 B2* | 1/2012 | Wallace | A61N 1/36082 607/2 |
| 8,209,027 B2* | 6/2012 | Butson | A61N 1/0534 600/407 |
| 8,216,173 B2 | 7/2012 | Dacey, Jr. et al. | |
| 8,282,593 B2 | 10/2012 | Dacey, Jr. et al. | |
| 8,333,753 B2* | 12/2012 | Nishtala | A61M 27/00 604/541 |
| 8,343,086 B2 | 1/2013 | Dacey, Jr. et al. | |
| 8,346,365 B2 | 1/2013 | Lozano | |
| 8,366,652 B2 | 2/2013 | Dacey, Jr. et al. | |
| 8,417,345 B2* | 4/2013 | Machado | A61N 1/0534 607/116 |
| 8,731,674 B2* | 5/2014 | Wallace | A61N 1/36082 607/116 |
| 8,798,754 B2* | 8/2014 | Knudson | A61N 1/0551 607/45 |
| 9,352,145 B2* | 5/2016 | Whitehurst | A61N 1/0531 |
| 2003/0088245 A1* | 5/2003 | Woloszko | A61B 18/148 606/41 |
| 2007/6090974 | 3/2007 | Lozano | |
| 2009/0125080 A1 | 5/2009 | Montgomery | |
| 2010/0234792 A1 | 9/2010 | Dacey, Jr. et al. | |
| 2010/0234793 A1 | 9/2010 | Dacey, Jr. et al. | |
| 2010/0240017 A1 | 9/2010 | Dacey, Jr. et al. | |
| 2010/0241048 A1 | 9/2010 | Dacey, Jr. et al. | |
| 2010/0241050 A1 | 9/2010 | Dacey, Jr. et al. | |
| 2010/0241051 A1 | 9/2010 | Dacey, Jr. et al. | |
| 2010/0241052 A1* | 9/2010 | Dacey, Jr. | A61L 2/0011 604/9 |
| 2010/0241053 A1 | 9/2010 | Dacey, Jr. et al. | |
| 2010/0249692 A1 | 9/2010 | Dacey, Jr. et al. | |
| 2010/0292629 A1 | 11/2010 | Dacey, Jr. et al. | |
| 2014/0243714 A1* | 8/2014 | Ward | A61B 5/04 601/2 |

OTHER PUBLICATIONS

Laxton, et al (2013) Deep Brain Stimulation for the Treatment of Alzheimer Disease and Dementias. World Neurosurgery 80 (3/4), S28.e1-8.

* cited by examiner

METHODS AND SYSTEMS FOR INTRAVENTRICULAR BRAIN STIMULATION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.5

BACKGROUND

Field

This disclosure relates to methods and systems for treatment of neurological disorders, and particularly for treating brain disorders using electrodes.

Description of the Related Art

Brain stimulation has been shown to be effective for the treatment of Parkinson's Disease and other movement disorders, Epilepsy, and Depression. Brain stimulation has the potential to be an effective treatment for numerous other disorders. Recently brain stimulation has been shown to be effective in enhancing memory when targeted at a component of the Papez circuit, a memory circuit of the brain, including the hippocampus, fornix, anterior thalamus etc. Clinical trials have been initiated to investigate fornix stimulation for Alzheimer's disease and its precursor, mild cognitive impairment (MCI). Furthermore, Lozano has also proposed stimulation of the anterior nucleus of the thalamus as another target for Alzheimer's disease and MCI.

Idiopathic Normal Pressure Hydrocephalus (NPH) is another neurological disorder that may be related to dementia, MCI, and Alzheimer's disease. NPH, however, is treated differently than the proposed treatment for MCI and Alzheimer's disease. The mainstay of treatment for NPH is the use of a ventricular shunt to divert cerebral spinal fluid (CSF) to the peritoneum, atrium, or pleural space. It is thought that the size of the ventricles in NPH is greater than the expected ventricular enlargement due to brain atrophy called hydrocephalus ex vacuo. By draining CSF, the size of the ventricles can be reduced and pressure on specific sensitive areas of the brain is thought to be reduced. NPH is typically associated with a triad of clinical symptoms, namely memory loss, gait instability, and urinary incontinence. Ventricular shunts have been shown to improve all three components of the clinical triad but are most successful and effective for gait and least effective for memory and cognitive changes. It has been proposed that NPH is an entity belonging to a spectrum of dementias. A recent study by Koivisto et al. (*Poor Cognitive Outcome in Shunt-Responsive Idiopathic Normal Pressure Hydrocephalus*. Neurosurgery 72(1):1-8 (2013)) demonstrated that while the diagnosis of NPH was not initially associated with dementia, a high number of patients with NPH that were treated with ventricular shunts later developed dementia including Alzheimer's disease. Given this association of NPH with dementia and Alzheimer's disease, it seems that the use of ventricular shunting for NPH is not effective in preventing the development of dementia and dementia related symptoms such as memory and cognitive decline in these patients.

SUMMARY

In accordance with one aspect of the present disclosure, there is provided a neuromodulation system configured to pass into, within, or through a ventricle in the brain, the system comprising one or more passageways for fluid; and an electrode or effector configured to modulate neural activity thereby modulating a neural state.

In some embodiments, the neural activity modulated can come from brain cells or neural fibers. In some embodiments, the neural activity can be at the fornix, the thalamus, the anterior nucleus of the thalamus, the circuit of Papez, and/or the hypothalamus. In some embodiments, the neural state can be an abnormal neural state, a seizure, epilepsy, Alzheimer's disease, Mild Cognitive Impairment, a normal neural state, Attention Deficit and Hyperactivity Disorder, stroke, multiple sclerosis, Parkinson's Disease, neural degenerative disease, cerebral palsy, schizophrenia, neuropsychiatric disorder, encephalopathy, and/or normal pressure hydrocephalus. In some embodiments, modulation of neural activity can comprise an increase in neural activity, a decrease in neural activity, and/or can lead to modulation of memory, attention, or concentration. In some embodiments, perforations in the passageway can permit cerebral spinal fluid to flow therethrough. In some embodiments, the perforations can be proximal to the electrode or effector, or distal to the electrode or effector, or both proximal and distal to the electrode or effector. In some embodiments, the electrode or effector is configured to pass through the foramen of Monroe. In some embodiments, the passageway can permit cerebrospinal fluid to flow out of the cranium to a reservoir. In some embodiments, the passageway is configured to permit cerebrospinal fluid to flow out of the cranium to a drain in a body cavity including the circulatory system, peritoneum, or pleural space, and wherein the passageway comprises a shunt. In some embodiments, the passageway is part of a shunt system with a valve controlling cerebrospinal fluid flow. In some embodiments, the passageway is configured so as to not be open to cerebrospinal fluid flow outside the cranium. In some embodiments, the passageway is configured to allow materials such as drugs, proteins, genes, viruses, particles, molecules, enhancers, etc. to flow into the ventricle. In some embodiments, the passageway comprises multiple compartments and is configured to allow bidirectional flow of fluid or materials. In some embodiments, the system can further include a controlled delivery pump to deliver materials through the passageway. In some embodiments, the passageway comprises an outer and inner surface forming a lumen. In some embodiments, the passageway comprises multiple lumens that are not enclosed similar to a Blake drain with an "X" or starfish cross sectional pattern. In some embodiments, the electrode or effector is located near an outer surface on the cross section of the catheter passageway to affect neural tissue. In some embodiments, the tip of the electrode or effector is curved to conform to the contour of the ventricular wall to reach the target neural structure. In some embodiments, the curved electrode or effector tip reaches both fornices by curving from one foramen of Monroe past the ipsilateral fornix to the contralateral fornix. In some embodiments, the system is configured to allow the electrode or effector to reach both the fornix and anterior nucleus of thalamus. In some embodiments, the electrode or effector is carried by a catheter, and wherein the catheter has adherence properties to maintain contact with neural structures on the wall of the ventricle. In some embodiments, the electrode or effector is carried by a catheter, and wherein the catheter uses mechanical properties to maintain contact with neural structures on the wall of the ventricle or foramen of Monroe. In some embodiments, the electrode or effector is carried by a catheter, and wherein the catheter diameter can be enlarged or decreased to better fit within the ventricle or foramen of Monroe so that the electrode or effector is in better contact with the neural structures on the wall of the ventricular system. In some embodiments, the electrode or effector is carried by a catheter, and wherein the catheter is inserted to the target using stereotactic guidance. In some embodiments, the electrode or effector is carried by a catheter, and wherein the catheter is inserted to the target using an endoscopic viewer. In some embodiments, the catheter or lumen is inserted to the target using fluoroscopic visualization guided by radio-opaque substance.

In accordance with another aspect, there is provided a neuromodulation system comprising one or more electrodes configured for intraventricular brain stimulation, and means for allowing cerebral spinal fluid flow during intraventricular placement of the one or more electrodes.

In some embodiments, the means for allowing cerebral spinal fluid flow can include a shunt catheter. In some embodiments, the means for allowing cerebral spinal fluid flow comprises one or more passageways. In some embodiments, the means for allowing cerebral spinal fluid flow comprises a Blake drain.

In accordance with another aspect, there is provided a method of modulating neural activity, the method comprising: providing a shunt electrode comprising an electrode and a passageway for fluid flow through the shunt electrode; inserting the shunt electrode into a brain; and modulating neural activity in the brain with the shunt electrode.

In some embodiments the neural activity modulated comes from brain cells or neural fibers. In some embodiments, the neural activity modulated is at the fornix, at the thalamus, at the anterior nucleus of the thalamus, within the circuit of Papez, and/or the hypothalamus. In some embodiments, prior to the modulating, the neural activity is in an abnormal state. In some embodiments, the abnormal neural state can be a seizure, epilepsy, Alzheimer's disease, Mild Cognitive Impairment, Attention Deficit and Hyperactivity Disorder, and/or encephalopathy. In some embodiments, prior to the modulating, the neural activity is in a normal neural state. In various embodiments, the modulation of neural activity can include an increase in neural activity, a decrease in neural activity, modulation of memory attention, or concentration. In some embodiments, perforations in the passageway permit cerebral spinal fluid to flow therethrough. In some embodiments, the passageway has perforations proximal to the electrode. In some embodiments, the passageway has perforations distal to the electrode. In some embodiments, the passageway has perforations both proximal and distal to the electrode for cerebrospinal fluid flow between compartments proximal and distal to the electrode. In some embodiments, the method includes inserting the shunt electrode through the foramen of Monroe In some embodiments, the passageway is configured to permit cerebrospinal fluid to flow out of the cranium to a reservoir. In some embodiments, the passageway is configured to permit cerebrospinal fluid to flow out of the cranium to a drain in a body cavity including the circulatory system, peritoneum, or pleural space. In some embodiments, the passageway includes a valve for regulating flow therethrough. In some embodiments, the passageway is configured so as to not be open to cerebrospinal fluid flow outside the cranium. In some embodiments, the method further includes flowing one or more of the following materials into the ventricle through the passageway: drugs, proteins, genes, viruses, particles, molecules, or enhancers. In some embodiments, the passageway comprises multiple compartments and allows bidirectional flow of the one or more materials. In some embodiments, the method further includes actively pumping the one or more materials through the passageway. In some embodiments, the passageway comprises an outer and inner surface forming a lumen. In some embodiments, the passageway comprises multiple lumens that are not enclosed. In some embodiments, the electrode is located near an outer surface of the shunt electrode. In some embodiments, the tip of the shunt electrode is curved to conform to the contour of the ventricular wall to reach the target neural structure. In some embodiments, the curved electrode or effector tip reaches both fornices by curving from one foramen of Monroe past the ipsilateral fornix to the contralateral fornix. In some embodiments, the shunt electrode comprises a catheter, wherein the catheter uses mechanical properties to maintain contact with neural structures on the wall of the ventricle or foramen of Monroe. In some embodiments, the shunt electrode comprises a catheter, and wherein the catheter diameter can be enlarged or decreased to better fit within the ventricle or foramen of Monroe so that the electrode or effector is in better contact with the neural structures on the wall of the ventricular system. In some embodiments, the shunt electrode comprises a catheter, and wherein the shunt electrode is inserted into the site in the brain using target stereotactic guidance.

DETAILED DESCRIPTION

The following detailed description presents various descriptions of specific embodiments of the invention. However, the invention can be embodied in myriad different ways as defined and covered by the claims as presented herein and as may be presented in the future.

Disclosed herein are devices and methods that can treat dementia in a manner that is safer than the current stimulation strategy for Alzheimer's disease and provides improved therapy for patients with NPH. Embodiments disclosed herein utilize brain stimulation of brain areas involved in memory and cognition through an intraventricular approach. In one embodiment, by combining the advantages of both brain stimulation and CSF flow in an intraventricular electrode having one or more passageways to permit fluid to flow therethrough. For example, an intraventricular electrode shunt catheter can be safely placed in any part of the ventricular system and through any foramen or aqueduct of the ventricular system without fear of obstruction to CSF flow. This combined approach has applicability to not only memory and cognitive related brain disorders such as Alzheimer's disease, NPH, MCI, but also epilepsy and seizures as well as neuropsychiatric disorders as well.

One strategy for the treatment of Alzheimer's disease using brain stimulation involves targeting the fornix bilaterally through bilateral deep brain stimulation. The targets chosen require placement of deep brain stimulation electrodes through brain parenchyma close to delicate areas such as the hypothalamus. In contrast, the placement of ventricular shunts involve the placement of a ventricular shunt catheter through a shorter and safer stretch of cortical brain tissue to access the ventricle near the foramen of Monroe, which is the junction or portal between the lateral ventricle and the third ventricle. The ventricular system of older individuals with brain atrophy typically is enlarged due to ex vacuo dilatation. This enlargement allows easy access to the ventricle and intraventricular structures. Brain atrophy also makes accurate placement of deep brain stimulation electrodes into intraparenchymal targets less accurate due to brain shift and brain sag during surgery thus raising the risk of complications. Thus an intraventricular approach optimizes the fortuitously large ventricles in these patients while avoiding the risks and complications associated with placing electrodes within neural tissue, particularly near eloquent and important areas such as the hypothalamus and thalamus and in more fragile tissue of the atrophic brain.

The fornix, a key relay structure in the memory circuit and the main output pathway of the hippocampus, converges to form the roof of the foramen of Monroe. At this location the fornix of both sides come close together and run side by side. Thus this is an ideal target in some embodiments for brain stimulation because a single unilateral electrode can stimulate the fornix bilaterally at this location.

The difficulty with intraventricular brain stimulation of the fornix at the foramen of Monroe (FM) is that the foramen of Monroe is a small portal through which the cerebral spinal fluid made in the lateral ventricles traverse to drain into the third ventricle. If the FM is blocked or occluded, the patient could develop obstructive hydrocephalus, a potentially lethal condition. Thus a deep brain stimulation electrode placed in or near the fornix may lead to obstruction of the FM through scarring of tissues and choroid around the electrode.

One of the approaches disclosed herein is to combine the brain stimulation electrode with a ventricular shunt allowing cerebral spinal fluid flow through the novel brain stimulation electrode. In this manner the electrode can be placed through the FM from the lateral ventricle into the third ventricle. The electrode can also sit within the FM. Since the fornix from both sides of the brain come together to meet side by side near the FM, stimulation of both fornices can be accomplished by a single unilateral electrode at the FM or in the third ventricle. Additionally, the electrode components can be embedded not only within the shunt lumen but also can be placed within the wall of the shunt catheter, wherein the electrode components are then closer to the white matter tissue and brain tissue by being on the outer surface of the electrode-catheter. Furthermore, the shunt catheter diameter can be chosen or adjusted to "fit" into the size of the FM without fear of blocking the flow of CSF. By fitting the size of the shunt, the electrode components within the shunt catheter or the wall of the shunt catheter are then brought closer to the neural tissue near the surface of the ventricle such as the fornix, fornices, thalamus, hypothalamus, hippocampus, etc, then stimulation of the neural elements is more effective.

Stenting electrodes similar to those designed for cardiac pacing and defibrillation through an intravascular approach are also applicable in this situation with or without a shunt pathway for CSF diversion. One preferred embodiment is a stent electrode system that allows free CSF flow through the electrode system. Multiple designs for intravascular stenting electrodes have been proposed for cardiac and intravascular stimulation. Such embodiments can be applied to the intraventricular context, particularly in a trans-foramen of Monroe placement. These embodiments include wire electrodes that have a loose spring and are released upon removal of an outer carrier/introducer tube or device. Another embodiment is a mesh that expands when released from a carrier/introducer.

Another embodiment includes a blind shunt catheter that allows drainage and CSF flow between the different parts of the ventricular system that the electrode catheter is placed within and between. The term "blind" is used because in this case, CSF is not diverted out of the cranium, only between different intracranial compartments. An example of this placement is the foramen of Monroe and the blind shunt catheter portion would allow communication between the lateral and third ventricles, having passageways for CSF flow both in the area distal and proximal to the electrode situated in the foramen of Monroe.

Figure 3A:
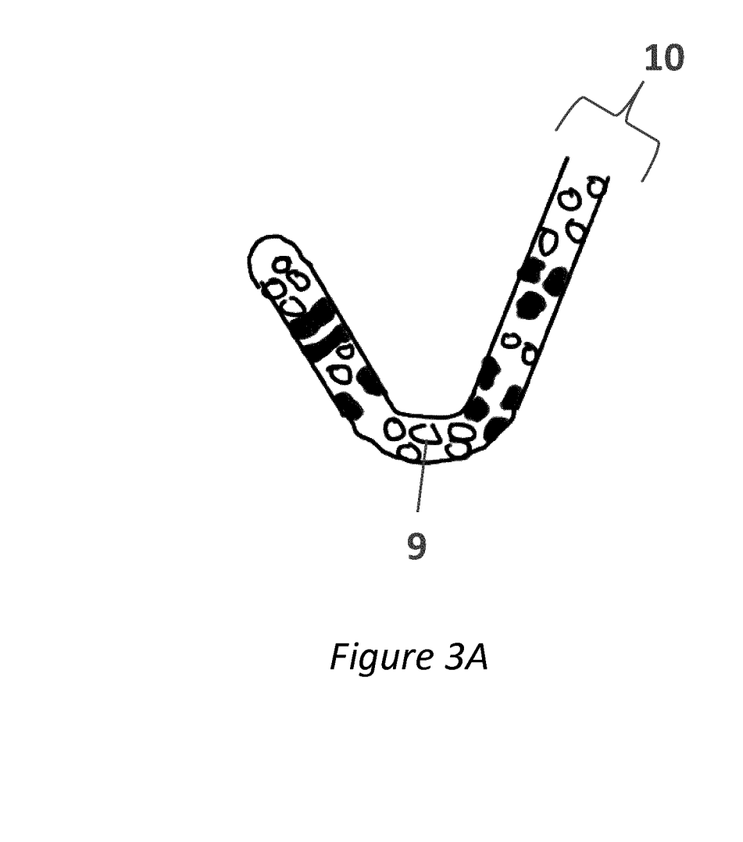
FIGS. 3A and 3B illustrate an electrode catheter in curved and straight configurations, respectively.
Figure 3B:
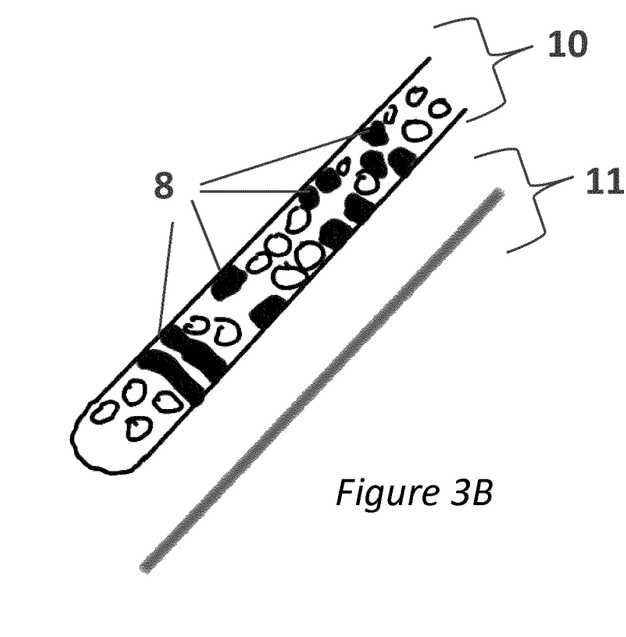

The tip of the catheter electrode preferably also has a shape that can curve through the FM of the ipsilateral side into the third ventricle and sit underneath both fornices. In some embodiments, the curve can be built into the shunt or electrode catheter and elicited when a straight guidewire is removed as shown in FIG. 3A and FIG. 3B. Alternatively the curve can be shapened or customized on an individual basis during the insertion process to customize the curvature to each individual's anatomy, in order to access both fornices. Bendable and malleable materials such as nitinol, which changes shape based on temperature or other conditions, e.g. electrical charge, or mechanical manipulation, is ideal for such applications to customize the curvature of the electrode within the ventricle. Precurved or preshaped catheter shapes that are inserted using a straight inner stylet also permit straight placement through the cortex, ventricle and foramen of Monroe, and once the catheter near final position through the foramen of Monroe, the natural curve can be "released" by removing the inner stylet.

Normal electrodes such as those used for deep brain stimulation (DBS) implanted into brain parenchyma cannot be bent or curved especially during the process of insertion or after insertion because any change in shape may cut, damage, compress, and/or destroy the brain tissue surrounding the tip. However since the shunt/electrode can be disposed within the ventricular system where cerebral spinal fluid (CSF) resides, only CSF will be displaced with alterations of the tip or shaft of the shunt electrode catheter.

Typically straight electrodes such as the DBS electrode or electrodes with a constant shape are placed stereotactically through predefined trajectories and paths based on a frame-based or frameless stereotactic system. Frameless systems, which allow minor changes during electrode placement, still are limited in the amount of change in trajectory after insertion through brain or neural tissue because any significant change may cause damage to neural tissue by slicing through the brain or compressing the brain tissue. In contrast, intravascular or endovascular procedures such as vascular stenting, cardiac angioplasty and stenting, and brain coiling of aneurysm and treatment of AVM's use a nonstereotactic freehand approach. These endovascular techniques use radiographic contrast material under fluoroscopic guidance to guide the catheter tip through the different venous or arterial branches to reach the target. Embodiments of the present invention allow both a stereotactic approach in the planning of the trajectory into the ventricular system and near the FM, but also allow a freehand intraventricular guidance by contrast medium under fluoroscopy similar to endovascular approaches. This fluoroscopic guidance is possible because ventriculography has been a standard method used for localization of structures around the ventricles. In fact, ventriculography was the main method of localization in the brain before CT and MRI scans were developed. Thus using intraventricular fluoroscopic guidance, the shunt electrode catheter can be placed through the FM and into the third ventricle and even through the FM on the contralateral side. Also the shunt electrode catheter can be used to access any surface of the lateral or third ventricle. Some cases of intraventricular guidance through the aqueduct of sylvius into the fourth ventricle have been reported as well. Thus this cannulation of the aqueduct of sylvius by a shunt electrode catheter is applicable with embodiments of the current invention as well.

In addition to fluoroscopic guidance, endoscopy is also commonly used for intraventricular procedures such as third ventriculostomy, resection of colloid cysts, and intraventricular tumors. Thus, endoscopic guidance of the shunt electrode catheter allows precise placement of the catheter through the FM into nearly any surface of the lateral, third, and fourth ventricles. Preferably, the stylet within the shunt electrode catheter is equipped for endoscopic visualization, e.g., it is an endoscope or has a miniature camera on the tip such as a CCD camera, chip on the tip. This way when the electrode catheter is ideally placed, the endoscopic viewer (e.g., the endoscope or camera on the tip of the stylet) can be removed. The ventricular dilatation usually seen in patients with atrophy is advantageous for endoscopic approach through the ventricular system.

Placing electrodes within the ventricular system or along the wall of the ventricle requires the electrodes to be adhered to the ventricular wall, either by an adhesive or by a mechanical device. The adherence is preferably achieved by use of the hydrophobic and lipophilic properties of materials to adhere to neural tissue along the wall of the ventricular system. Other mechanisms for adhesion include mechanical adhesion, chemical adhesion, dispersive adhesion, electrostatic adhesion, and diffusive adhesion. One skilled in the art will recognize preferable methods to adhere an electrode onto the wall of the ventricle. However one advantage of embodiments of the present invention is to utilize the FM as an anchoring site for the electrode shunt catheter. Because of the shunting capability, obstruction to CSF flow is prevented and the electrode shunt catheter can use at least mechanical adhesion to contact and stay in contact with a particular ventricular surface.

Furthermore, the anterior thalamic nucleus makes up the lateral wall of the inferior FM and third ventricle. The anterior thalamus has been a target for not only epilepsy but also Alzheimer's disease and other cognitive disorders such as mild cognitive impairment (MCI). Thus an accurately placed electrode shunt catheter can access both the fornix and the anterior thalamus through an intraventricular approach that spares damage to the nuclei. This approach is advantageous because the anterior thalamic nucleus is difficult to access because it is typically shielded by the lateral ventricle and thus typical electrode placements into the anterior nucleus pass through the ventricle as well as a plexus of blood vessels near the ventricular walls. Thus an intraventricular access to the anterior nucleus requires only an entry into the ventricle at a safe entry point, i.e., that used for shunt catheter placement, and eliminates a second ventricular wall penetration required for typical anterior thalamic nucleus access. Other targets accessible from an intraventricular approach include but are not limited to the following: fornix, thalamus, anterior nucleus of thalamus, medial dorsal thalamic nucleus, anterior commissure, posterior commissure, mammillary bodies, hypothalamus.

Specifically, since the fornices comprise the superiomedial and anteriomedial walls of the FM, the electrode shunt catheter placed through the FM is ideally situated to interact with the FM. This interaction can include electrical stimulation or electrical recording. Other methods of interaction include cooling or heating, electrical field generation and stimulation, opticogenetic methods, laser methods, fluorescence methods, ultrasonic methods, direct electrical current stimulation, and mechanical stimulation or disruption. Since the fornix is the main output pathway of the hippocampus and a main fiber tract for circuit of Papez, stimulation and recording here is beneficial for treating a number of disorders including memory dysfunction such as Alzheimer's Disease, Normal Pressure Hydrocephalus, epilepsy, and depression. Accessing the fornix through an intraventricular approach is safer than the traditional direct intraparenchymal approach because the electrode currently passes through brain tissue throughout the entire tract and often through or close to important structures such as the hypothalamus. Instead, the intraventricular approach only passes through a small region of brain tissue, in the same safe manner that ventricular shunts are placed, with minimized risk to the deeper critical brain areas. Also, an intraventricular approach to the fornix at the area of the FM allows both fornices to be accessed using a unilateral approach, thereby eliminating half of the risk of the surgery, i.e. drilling a second burrhole and passing a second electrode on the contralateral side.

Figure 1:
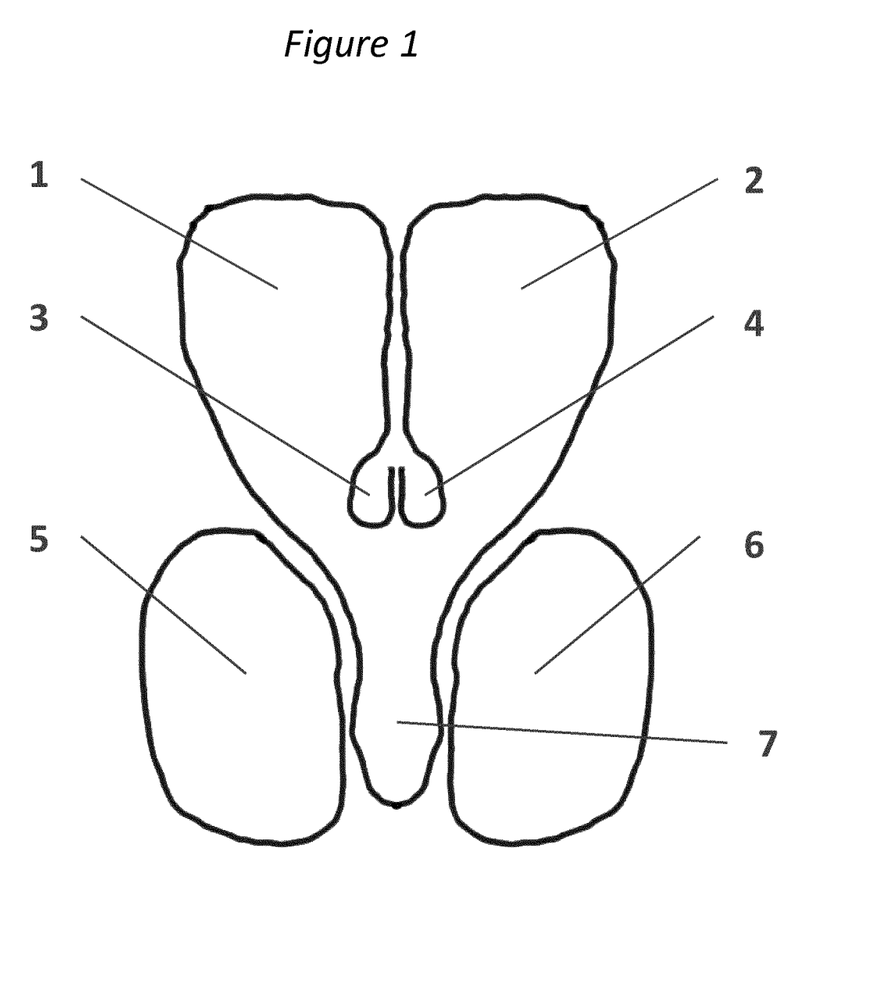
FIG. 1 is a schematic diagram of the ventricular system.

FIG. 1 is a schematic diagram of the ventricular system showing right (1) and left (2) lateral ventricles, right (3) and left (4) fornices, third ventricle (7), and right (5) and left (6) thalami.

Figures 2A, 2B:
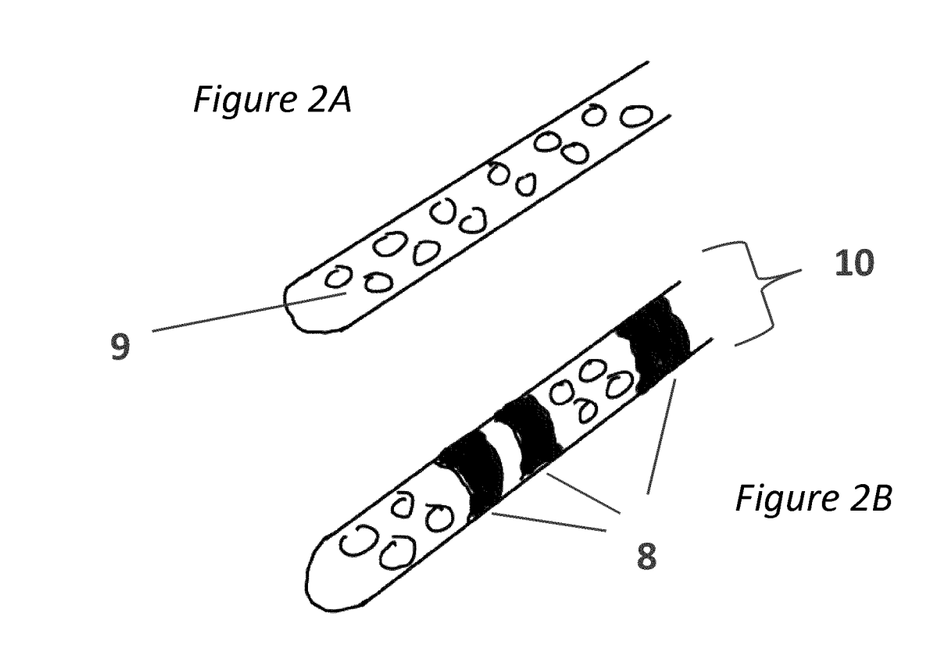
FIGS. 2A and 2B illustrate shunt and electrode catheters, respectively.

FIGS. 2A and 2B illustrate a straight shunt (FIG. 2A) and electrode catheter (FIG. 2B). FIG. 2A shows a typical shunt cather or ventriculostomy catheter that is a hollow tube with perforations (9). The perforations (9) allow drainage of CSF through the hollow tube or channel to the shunt and distal drainage site (usually the peritoneum, atrium of the heart, or pleural cavity). FIG. 2B shows a combination electrode catheter (10) system with electrodes embedded into a catheter with perforations similar to a shunt catheter such that CSF can flow from one ventricle to another while the electrode contacts (8) are near a site nearby the ventricular system such as the fornix and thalamus. The perforations prevent blockage of CSF flow when the electrode catheter passes through the foramen of Monroe.

Figure 4:
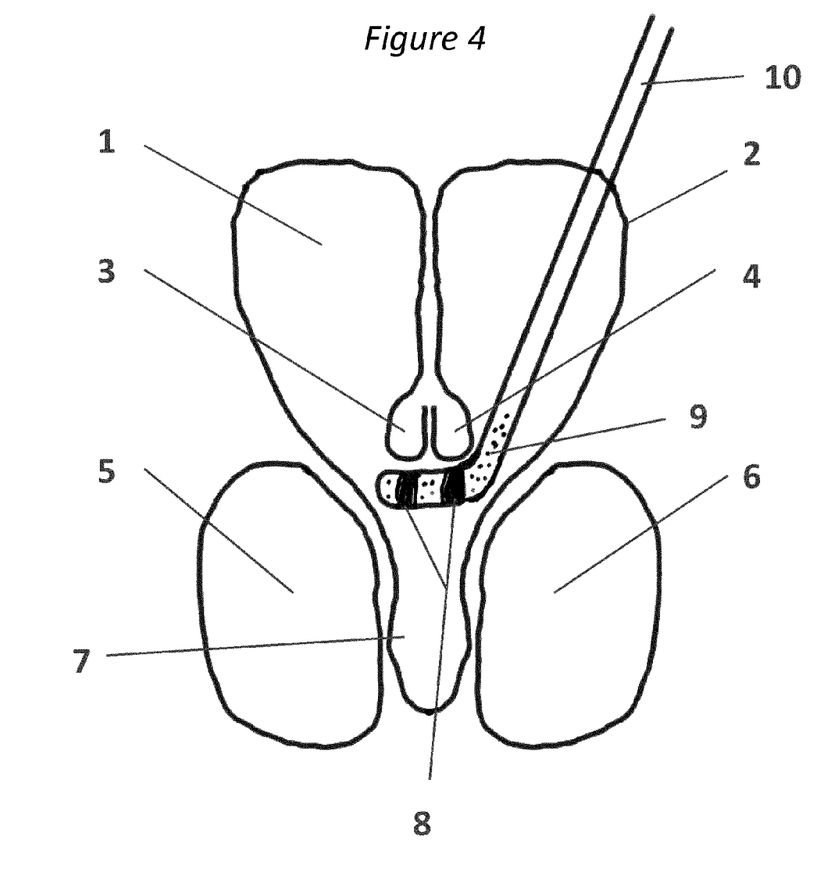
FIG. 4 illustrates a ventricular catheter electrode inserted into the brain.
Figure 5:
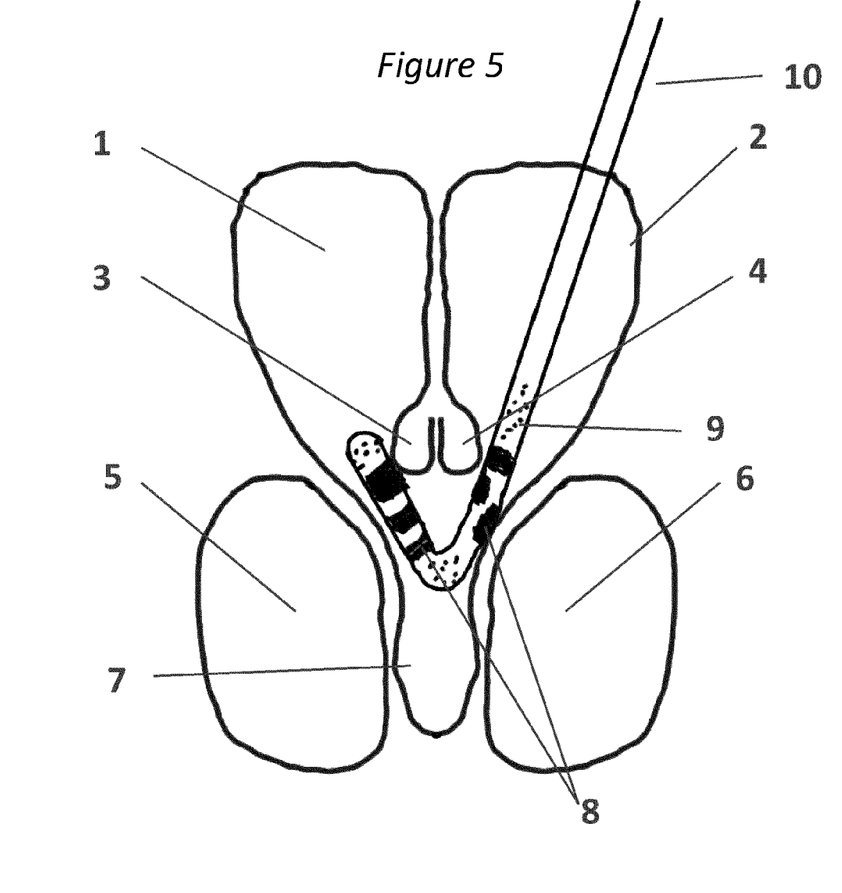
FIG. 5 illustrates a "V" curved ventricular electrode catheter inserted into the brain.

FIG. 3A illustrates one embodiment of a curved electrode catheter. As illustrated, an electrode catheter (10) can be preshaped into a bent configuration so that the electrode catheter can pass through one lateral ventricle through the foramen of Monroe into the third ventricle to the contralateral lateral ventricle through the contralateral foramen of Monroe. FIG. 3B shows that a straight rigid stylet (11) can be inserted into the lumen of the electrode catheter to straighten the prebent, naturally curved electrode during insertion. As the electrode is placed through the foramen of Monroe into the third ventricle, the stylet is pulled back and the prebent shape of the electrode naturally curves into the opposite foramen of Monroe into the contralateral lateral ventricle, as shown in FIGS. 4 and 5. The electrodes (8) shown can be both circumferential around the catheter or localized and distributed around the catheter for more focused current steering capabilities.

FIG. 4 illustrates the ventricular catheter electrode (10) passing through the left ventricle (2) and entering the third ventricle (7) through the foramen of Monroe (not lumbered). The electrode catheter (10) is curved under the left (4) and right (3) fornices. Perforations (9) allow free flow of CSF between the right ventricle (1), left ventricle (2), third ventricle (7) and shunt catheter (10). Electrodes (8) allow stimulation and interaction with both left (4) and right (3) fornices through a single passage of the electrode catheter through a single burrhole and a single side.

FIG. 5 illustrates one embodiment of a "V" curved ventricular electrode catheter (10). The sharper bend allows electrode contacts (8) to access the left fornix (4), right fornix (3), left thalamus (6), and right thalamus (5) all through a single electrode catheter and a single burrhole on a single side. The perforations (9) allow free CSF flow through the left ventricle (2), right ventricle (1), and third ventricle (7). The shunt catheter (10) also allows CSF to drain outside the cranium as in a ventriculo-peritoneal (-atrial or -pleural) shunt when CSF diversion is necessary.

Figures 6A, 6B, 6C, 6D:
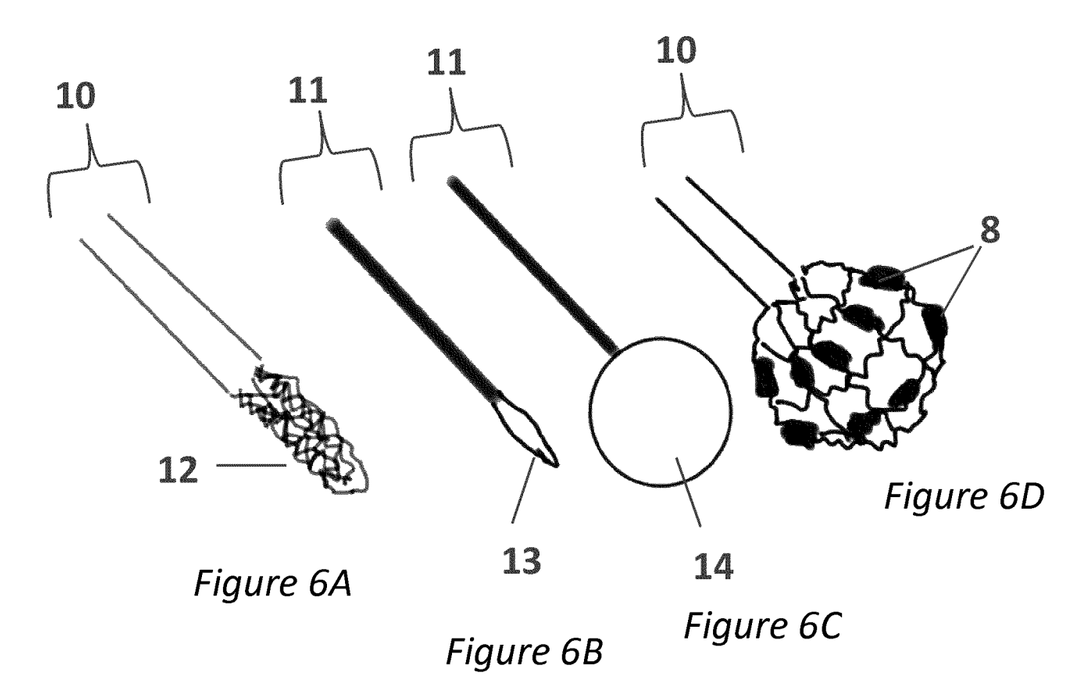
FIGS. 6A-6D illustrate embodiments of an expandable electrode system.

FIGS. 6A-6D illustrate embodiments of an expandable electrode system. FIG. 6A shows an electrode catheter with an expanded mesh tip (12) that is collapsed for safe insertion through brain tissue. FIG. 6B shows a sylet (11) designed to be placed within the lumen of the electrode catheter (10). The expansion mechanism, here being an inflatable balloon (13) is deflated. FIG. 6C shows the expansion mechanism of the inner stylet (11) fully expanded, here being an inflatable balloon. FIG. 6D shows an expandable electrode system that has been fully expanded from the expansion of the expansion mechanism that has now been deflated and withdrawn from the lumen.

Figure 7:
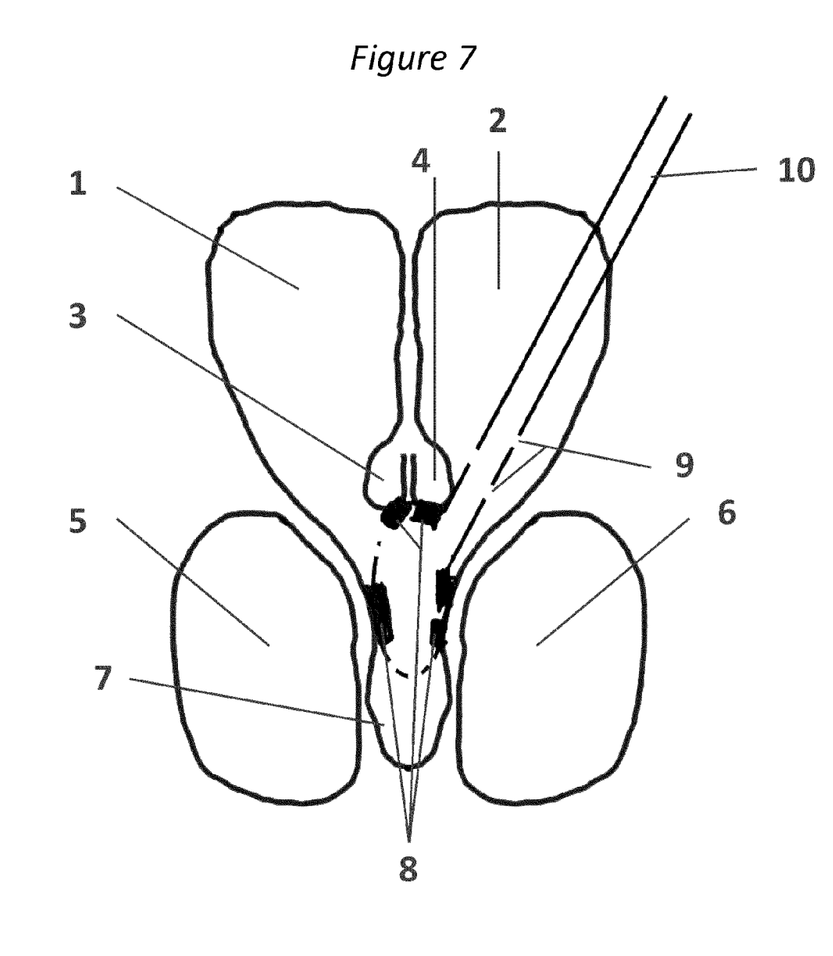
FIG. 7 illustrates an expandable electrode system inserted into the brain.

FIG. 7 illustrates an expandable electrode system (10) showing the electrode catheter (10) passing through the left lateral ventricle (2) through the foramen of Monroe (not labeled) and into the third ventricle (7). The expandable electrode system is expanded (through one of several state of the art techniques including a balloon expansion system shown in FIGS. 6A-6D). The electrodes (8) are positioned on the surface of the mesh to contact the fornices (3, 4) and thalami (5, 6). Perforations or openings in the mesh (9) allow free CSF flow between the ventricular systems.

Figure 8:
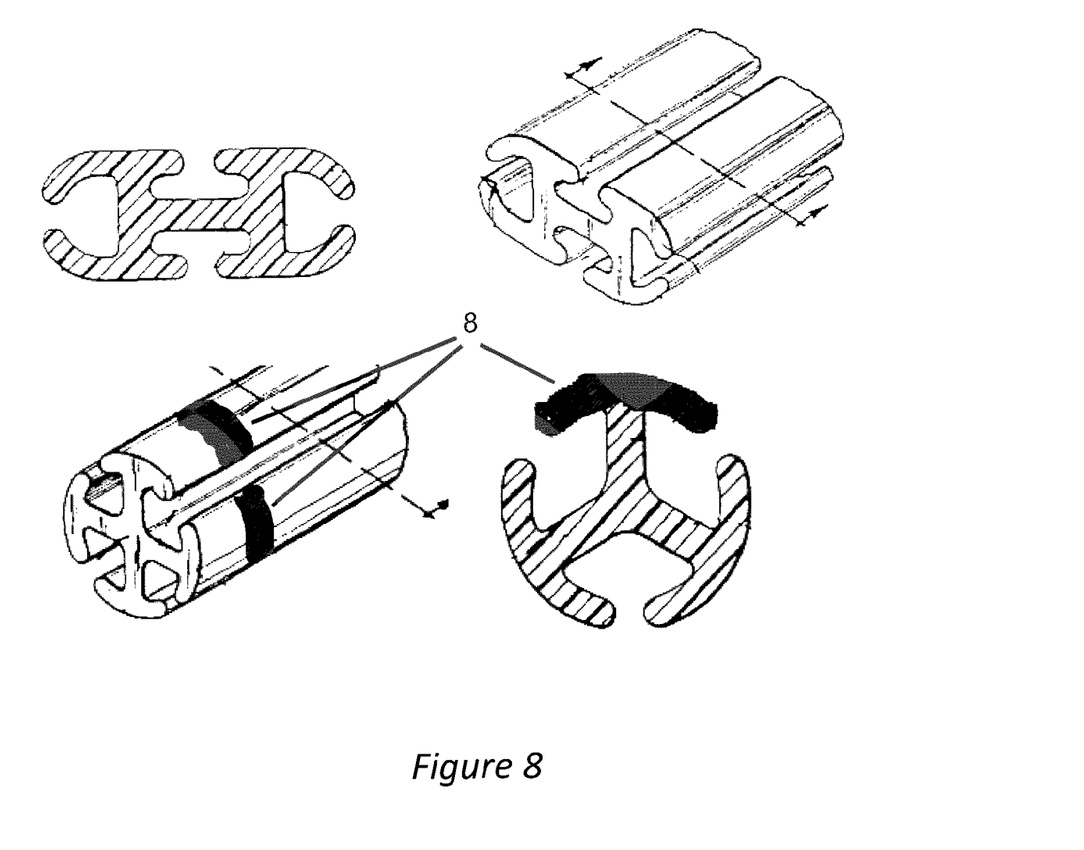
FIG. 8 illustrates examples of Blake drains with embedded electrodes.

FIG. 8 illustrates examples of Blake drains which allow fluid flow through the catheter without a closed lumen. Electrodes (8) are located at the outer surfaces of the drains but can also be located within the inner areas of the catheter for current steering.

In addition to shunt catheters with electrode or effectors within the wall of the shunt catheter, other embodiments are also envisioned. Cardiac stent electrodes have been proposed for intravascular cardiac pacing and defibrillation. These expandable wire mesh electrodes allow blood to run through the mesh electrode while expanding to the wall of the blood vessel to stimulate cardiac pacing structures just outside the vascular wall. This type of mesh electrode system would also work for the cerebral ventricular system where wire mesh electrodes expand to fill the foramen of Monroe and/or the third ventricle. In this manner, bilateral thalamic (Anterior and Dorsal Medial Nuclei) and hypothalamic nuclei can be accessed and modulated. Aside from electrodes designed for cardiac and vascular use, any type of drain used surgically to drain fluid from the body can be used as a passageway for CSF. The type of drains include Blake type drains (see FIG. 8) which do not have an inner and outer surface since geometrically they have a cross sectional shape of a star and the fluid flows in between the arms of the star formation. The effectors or electrodes of this embodiment would be located anywhere along the inside of the drain including the tips of the star but could also have effectors or electrodes in the middle of the star at the junction of the arms so that current can be directed (steered) outwardly from the middle of the catheter outwards towards brain tissue.

Although this invention has been described in terms of certain embodiments, other embodiments that are apparent to those of ordinary skill in the art, including embodiments that do not provide all of the features and advantages set forth herein, are also within the scope of this invention. Moreover, the various embodiments described above can be combined to provide further embodiments. In addition, certain features shown in the context of one embodiment can be incorporated into other embodiments as well. Accordingly, the scope of the present invention is defined only by reference to the appended claims or by claims as presented in the future.

What is claimed is:

1. A method of modulating neural activity, the method comprising:
   providing a shunt electrode comprising an electrode and a passageway for fluid flow through the shunt electrode;
   inserting the shunt electrode into a brain;
   advancing the tip of the shunt electrode and curving it to conform to the contour of the ventricular anatomy;
   curving the tip of the shunt electrode to reach both fornices by curving from one foramen of Monroe past the ipsilateral fornix to the contralateral fornix; and
   modulating neural activity in the brain with the shunt electrode.

2. The method of claim 1, wherein the neural activity modulated comes from one of more of the following: brain cells, neural fibers, fornix, thalamus, anterior nucleus of thalamus, a structure within the circuit of Papez, and hypothalamus.

3. The method of claim 1, wherein prior to the modulating, the neural activity is in one or more of the following neural states: a normal neural state, an abnormal neural state, an abnormal neural state related to seizure, an abnormal neural state related to epilepsy, an abnormal neural state related to Alzheimer's disease, an abnormal neural state related to Mild Cognitive Impairment, an abnormal neural state related to Attention Deficit and Hyperactivity Disorder, an abnormal neural state related to encephalopathy, an abnormal neural state related to stroke, an abnormal neural state related to Parkinson's Disease, an abnormal neural state related to neurodegenerative disease, an abnormal neural state related to cerebral palsy, an abnormal neural state related to schizophrenia, an abnormal neural state related to neuropsychiatric disorder.

4. The method of claim 1, wherein the modulation of neural activity comprises one or more of the following: an increase in neural activity, a decrease in neural activity, a modulation of memory, attention, or concentration.

5. The method of claim 1, wherein perforations in the passageway permit cerebral spinal fluid to flow therethrough.

6. The method of claim 1, wherein the passageway has perforations proximal to the electrode, distal to the electrode, or both proximal and distal to the electrode for cerebrospinal fluid flow between compartments proximal and distal to the electrode.

7. The method of claim 1, comprising inserting the shunt electrode through the foramen of Monroe.

8. The method of claim 1, wherein the passageway is configured to permit cerebrospinal fluid to flow out of the cranium to a reservoir.

9. The method of claim 1, wherein the passageway is configured to permit cerebrospinal fluid to flow out of the cranium to drain into a body cavity including the circulatory system, peritoneum, or pleural space and wherein the passageway comprises a shunt system with a valve controlling cerebrospinal fluid flow.

10. The method of claim 1, wherein the passageway is configured so as to not be open to cerebrospinal fluid flow outside the cranium.

11. The method of claim 1, wherein the shunt electrode comprises a catheter, wherein the catheter uses mechanical properties to maintain contact with neural structures on the wall of the ventricle or foramen of Monroe.

12. The method of claim 1, wherein the shunt electrode comprises a catheter, and wherein the catheter diameter can be enlarged or decreased to better fit within the ventricle or foramen of Monroe so that the electrode or effector is in better contact with the neural structures on the wall of the ventricular system.

13. The method of claim 1, wherein the shunt electrode comprises a catheter, and wherein the shunt electrode is inserted into the target site in the brain using one or more of the following means: stereotactic guidance, an endoscopic viewer, fluoroscopic visualization guided by radio-opaque substance, and ventriculography.

\* \* \* \* \*

UNITED STATES PATENT AND TRADEMARK OFFICE
CERTIFICATE OF CORRECTION

PATENT NO.         : 9,919,146 B2
APPLICATION NO.    : 14/266732
DATED              : March 20, 2018
INVENTOR(S)        : Sherwin Hua Page 1 of 1

It is certified that error appears in the above-identified patent and that said Letters Patent is hereby corrected as shown below:

In the Specification

In Column 1 at Line 11, Change "37 CFR 1.5" to --37 CFR 1.57.--.

In Column 8 at Lines 5-6, Change "superiomedial and anteriomedial" to --superomedial and anteromedial--.

In Column 8 at Line 11, Change "opticogenetic" to --optogenetic--.

In Column 8 at Line 39, Change "cather" to --catheter--.

In Column 9 at Line 24, Change "sylet" to --stylet--.

In the Claims

In Column 10 at Line 35, In Claim 2, change "one of more" to --one or more--.

Signed and Sealed this
Tenth Day of July, 2018

Andrei Iancu
*Director of the United States Patent and Trademark Office*